United States Patent [19]
Tsubota et al.

[11] Patent Number: 5,587,296
[45] Date of Patent: Dec. 24, 1996

[54] REAGENT FOR ASSAYING GLUCOSE

[75] Inventors: Hiroyuki Tsubota; Reiko Shimada, both of Tokyo, Japan

[73] Assignee: Iatron Laboratories, Inc., Tokyo, Japan

[21] Appl. No.: 424,284

[22] PCT Filed: Aug. 24, 1994

[86] PCT No.: PCT/JP94/01395

§ 371 Date: Apr. 21, 1995

§ 102(e) Date: Apr. 21, 1995

[87] PCT Pub. No.: WO95/06136

PCT Pub. Date: Mar. 2, 1995

[30] Foreign Application Priority Data

Aug. 25, 1993 [JP] Japan ................... 5-232371

[51] Int. Cl.$^6$ .................. C12Q 1/54; C12Q 1/50; C12Q 1/32; G01N 33/48
[52] U.S. Cl. .................. 435/14; 435/17; 435/26; 435/2; 435/4; 436/63; 436/74
[58] Field of Search .................. 435/14, 17, 26, 435/2, 4; 436/63, 74

[56] References Cited

U.S. PATENT DOCUMENTS 3,616,254 10/1971 Beutler .................. 435/14
4,042,462 8/1977 Johnson et al. .................. 435/14
4,189,536 2/1980 Green .................. 435/14
4,729,959 3/1988 Ryan .................. 435/14
4,897,346 1/1990 Gawronski .................. 435/14
5,168,046 12/1992 Hamamoto et al. .................. 435/14

FOREIGN PATENT DOCUMENTS 9401395 8/1994 Japan.

Primary Examiner—Gary E. Hollinden
Assistant Examiner—Louise Leary
Attorney, Agent, or Firm—Sughrue, Mion, Zinn, Macpeak & Seas

[57] ABSTRACT

A reagent for assaying glucose, which comprises a first liquid reagent having a pH of 7.5 to 9.5 and containing at least either glucokinase or hexokinase, glucose 6-phosphate dehydrogenase, and adenosine 5'-triphosphate and a second liquid reagent having a pH of 3 to 5 and containing the oxidized form of nicotinamide adenine dinucleotide phosphate. The reagent can be stored as such stably for long in or out of contact with light at normal or low temperatures, so that it can be stored for long in the site of clinical examination and applied to an automatic analyzer without the necessity for dissolution prior to use.

8 Claims, 3 Drawing Sheets

REAGENT FOR ASSAYING GLUCOSE

TECHNICAL FIELD

The present invention relates to a reagent for assaying glucose, more particularly, an improved liquid reagent for assaying glucose which is stable over a long period.

BACKGROUND ART

The assay of glucose in biological fluid, such as blood or urine is one of the important items in the diagnosis of diabetes, hypoglycemia, or other diseases, or the observation of progress in treatment. Nowadays, the methods for assaying glucose in clinical examinations may be roughly classified into reduction methods, enzymatic methods, condensation methods, simplified assay methods, and so on. The reduction methods have disadvantages in that other reduced substances in addition to glucose are measured. Thus, the enzymatic methods (glucose oxidase method), which are superior in specificity, were introduced in the 1950s. Further, the HK-G6PDH method using hexokinase (hereinafter referred to as HK) and glucose-6-phosphate dehydrogenase (hereinafter referred to as G6PDH) has been accepted as a standard method for assaying glucose with more specific manner.

Although the HK-G6PDH method is useful for obtaining accurate glucose level, the components of the reagent are unstable substances, and thus, a long term storage is difficult. Therefore, the enzymes, substrates and the like are generally supplied in the form of lyophilized products and used after dissolved in a buffer or the like at the time of use. However, there is a demand for stability of the reagent after dissolved, in view of the requirements for workability and cost. For example, Japanese Unexamined Patent Publication (Kokai) No. 56-140899 discloses a technique relating to the stability of a reagent for assaying glucose.

The above-mentioned Patent Publication (Kokai) No. 56-140899 describes a technique for enhancing the stability of the reagent by incorporating a sulfhydryl compound (for example, a reduced type of glutathione and N-acetyl cysteine) and/or a chelating agent (for example, EDTA, EGTA) and a bactericide and a pH buffer. The technique basically focuses on a reagent prepared by dissolving lyophilized products and improves the stability of the aqueous solution (solution B) of the components other than the coenzymes. The stability is maintained for at most about 10 days.

Further, Japanese Unexamined Patent Publication (Kokai) No. 63-24900 discloses a technique relating to a stable liquid enzyme composition for assaying glucose which can be stored for a long period of time (over one year). The reagent is a two-component reagent composed of an enzymatic component (hexokinase and G6PDH) and a coenzymatic component (ATP and NAD). The enzymatic component comprises approximately 20 to 40% (v/v) of a polyol organic solvent, a stabilizer such as EDTA, antioxidant such as albumin or poly(vinylpyrrolidone), and an agent for controlling a microorganism, such as sodium azide, and the pH is adjusted to approximately 7.5. Further, the coenzymatic component contains approximately 5 to 20% (v/v) of a polyol organic solvent, and the pH is adjusted to about 7.5.

However, the reagent per se containing a polyol (such as glycerol) is viscous. Further, if poly (vinylpyrrolidone) is added as an antioxidant, the viscosity of the reagent becomes higher. The high viscosity causes troubles in automatic analyzers, for example, a reduction of the accuracy of the amount of the reagents added. Further, there is the problem that the stability of the coenzymes, i.e., NAD and ATP, is insufficient.

Recently, it is desired to improve the workability for users, by providing the reagents in the form of liquid from a supplier. Further, such reagents are in many cases used in automatic analyzers, and therefore, it is necessary to reformulate the reagents as a two-component form and maintain the stability of the reagent compositions for a long period of time (for example, from half a year to one year).

The reaction formulas of the above HK-G6PDH method are as follows:

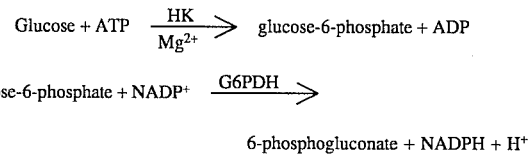

Glucose-6-phosphate + NADP⁺ $\xrightarrow{\text{G6PDH}}$ 6-phosphogluconate + NADPH + H⁺

In the above formulas, ATP stands for adenosine 5'-triphosphate, ADP stands for adenosine 5'-diphosphate, and NADP⁺ stands for the oxidized form of nicotinamide adenine dinucleotide phosphate.

Each of the components participating the above reactions has stability conditions different from each other. Therefore, depending on the combination of the components, the stability of the reagent for assaying glucose prepared by mixing the components sometimes becomes synergistically improved or sometimes conversely becomes worse.

Further, although the assay hitherto was manually performed by mixing a sample with a one-component reagent, a two-component reagent has recently become usual due to the spread of automatic analyzers. In most cases of such two-component reagents, an initiating reagent (second reagent) contains ATP which is the substrate of the initiating enzyme, and a first reagent contains all the remaining components. In some cases, an enzyme, such as HK or G6PDH (or both enzymes) is used as the second reagent, but there was a problem in the stability of the enzymes. Further, a sufficient storability was not able to be obtained even when ATP was used as the second reagent.

The stability of the enzymes has been improved by removing the interfering contaminant enzymes by sophisticated purification of the enzymes per se and by using heat resistant enzymes, for example, glucokinase (hereinafter referred to as GlcK) derived from *Batillus stearothermophilus*, HK obtained from recombinant yeast or chemically modified enzymes thereof, but it was difficult to obtain a good storage stability for liquid reagents as a whole.

Of the components other than the stabilized enzymes, each of coenzyme NADP⁺ and the substrate ATP are one of the greatest destabilizing factors. In particular, the deterioration of NADP⁺ is a factor obstructing storage stability.

The inventors of the present invention engaged in various in-depth studies to solve the above problems in the prior art and as a result discovered a reagent composition having sufficient storage stability as a liquid reagent. The present invention is based on this discovery.

DISCLOSURE OF THE INVENTION

The present invention relates to a reagent for assaying glucose characterized by comprising a first reagent containing at least one of glucokinase (GlcK) or hexokinase (HK), glucose 6-phosphate dehydrogenase (G6PDH), and adenosine 5'-triphosphate (ATP) and a second reagent containing an oxidized form of nicotinamide adenine dinucleotide phosphate (NADP⁺), the pH of the first reagent being 7.5 to 9.5, the pH of the second reagent being 3 to 5, and the two reagents being liquids.

BEST MODE FOR CARRYING OUT THE INVENTION

Figure 1:
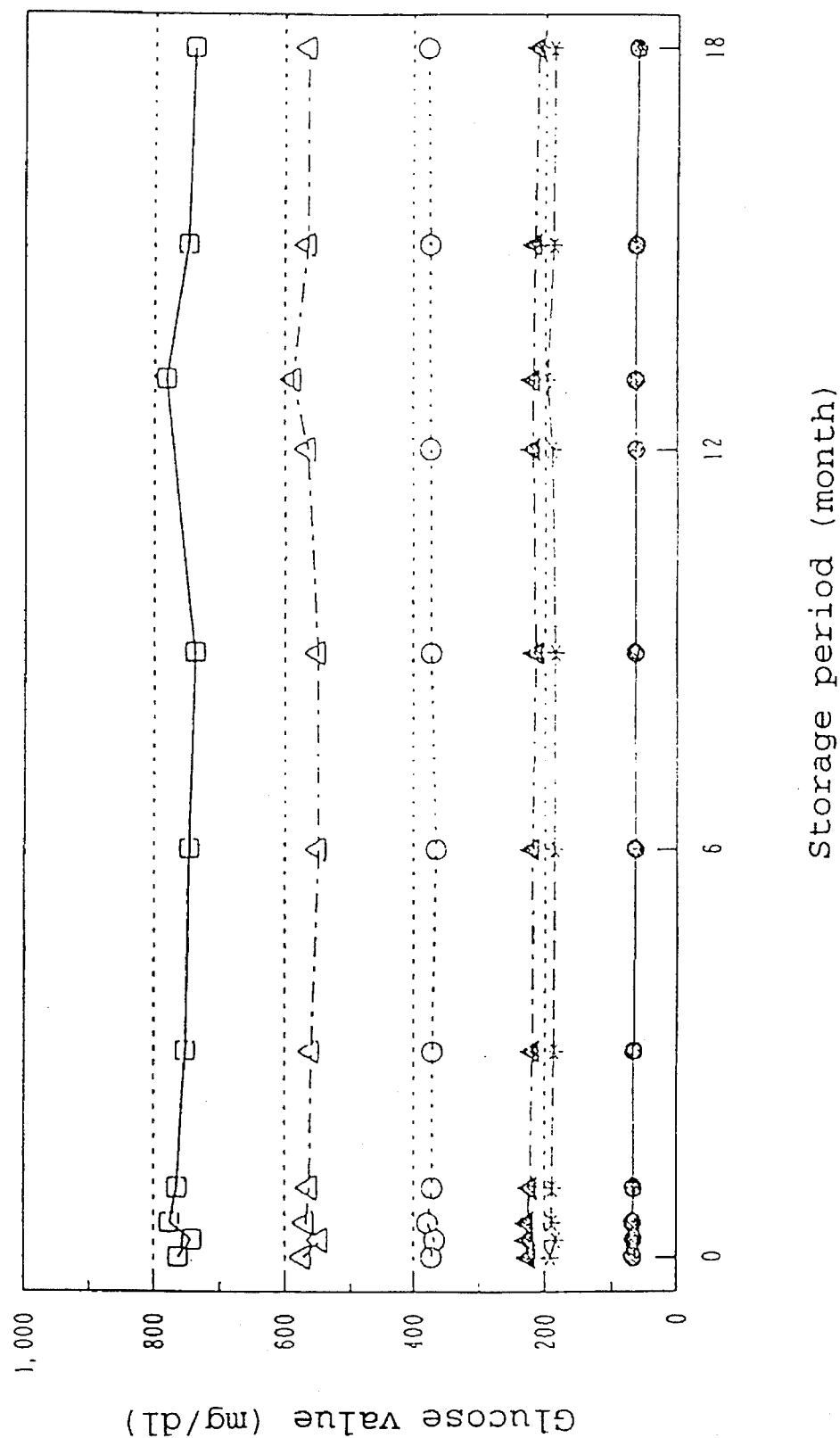
FIG. 1 is a graph showing the stability in the case of storage of the reagent of the present invention at 4° C.

The present invention will be explained hereinafter in detail.

Although, the conventional reagent for assaying glucose wherein HK and G6PDH were used was generally a one-component reagent, a two-component reagent has been prevailing along with the advances in automatic analyzers. In many conventional two-component reagents, ATP which is a coenzyme (substrate) of HK was used as an initiating reagent which reacts first with the substance (glucose) to be assayed. This is because that a sample blank can be subtracted after the G6PDH reaction by adding one of the initiating enzymes, HK and ATP, which react first with glucose, at a later step. Further, the reason for using ATP is that it is easier to handle than HK which is a protein.

The above concept was prevalent in the days when the degree of purification of enzymes was poor. At the present time, however, when highly purified enzymes and standard substrates are available, it is possible to highlight the establishment of stabler conditions. Accordingly, combination of reagent composition never before dreamed of in the past are now being developed.

The reagent for assaying glucose of the present invention comprise: p1 (1) a first liquid reagent having a pH of 7.5 to 9.5 and containing GlcK or HK, G6PDH and ATP, and (2) a second liquid reagent having a pH of 3 to 5 and containing NADP⁺.

The ATP contained in the first reagent is stable in an alkaline buffer of a pH of about 7.5 to 10 and thus, the first reagent is dissolved in a buffer of a pH of 7.5 to 9.5. A pH of over 9.5 is not preferable from the viewpoint of the stability of the enzyme. Any buffer normally used at the above range of pH values, for example, a tris(hydroxymethyl)aminomethane (hereinafter referred to as tris) buffer (pH 9.0) can be used as the above buffer.

As the HK and the GlcK, it is preferable to use enzymes having a pH stability in a weak alkali (pH 7 to 9.5), for example, HK derived from yeast or GlcK derived from *Batillus stearothermophilus*. The enzymes may be added in an amount that the enzymes are active. It is preferable to add at least 0.2 U of the enzyme. There is no particular upper limit, but in view of the cost or the like, the enzyme may be used in the range from 0.2 to 100 U.

As the G6PDH, an enzyme which has a pH stability in weak alkali (pH 7 to 9.5), for example, an enzyme derived from *Leuconostoc mesenteroides* is suitable. The enzyme may be added in an amount that the enzyme is active. It is preferable to add at least 0.5 U of the enzyme. There is no particular upper limit, but in view of the cost or the like, the enzyme may be used in the range from 0.5 to 100 U.

The ATP is preferably added in an amount of 0.5 to 5 mM, more preferably 1 to 3 mM. It is also possible to add to the first reagent, if necessary, magnesium salts, chelating agents, for example, ethylenediaminetetraacetic acid (hereinafter referred to as EDTA), or the like.

The NADP⁺ added to the second reagent is stable in an acidic buffer, and thus the NADP⁺ can be dissolved in a buffer of a pH of 3 to 5 to prepare the second reagent. Any buffer normally used at the above range of pH, for example, an acetate buffer (pH 4.0) may be used as the above buffer. The NADP⁺ can be preferably added in an amount of 1 to 20 mM, more preferably 5 to 10 mM. The second reagent may also contain a magnesium salt, if necessary. After the first reagent and the second reagent are mixed, the pH of the mixture is preferably adjusted approximately 7.5 to 8.5. The buffer concentrations of the first and the second reagents, and the ratios of the mixture thereof may be suitably adjusted.

EXAMPLES

The present invention now will be further illustrated by, but is by no means limited to, the following Examples:

Example 1

Figure 2:
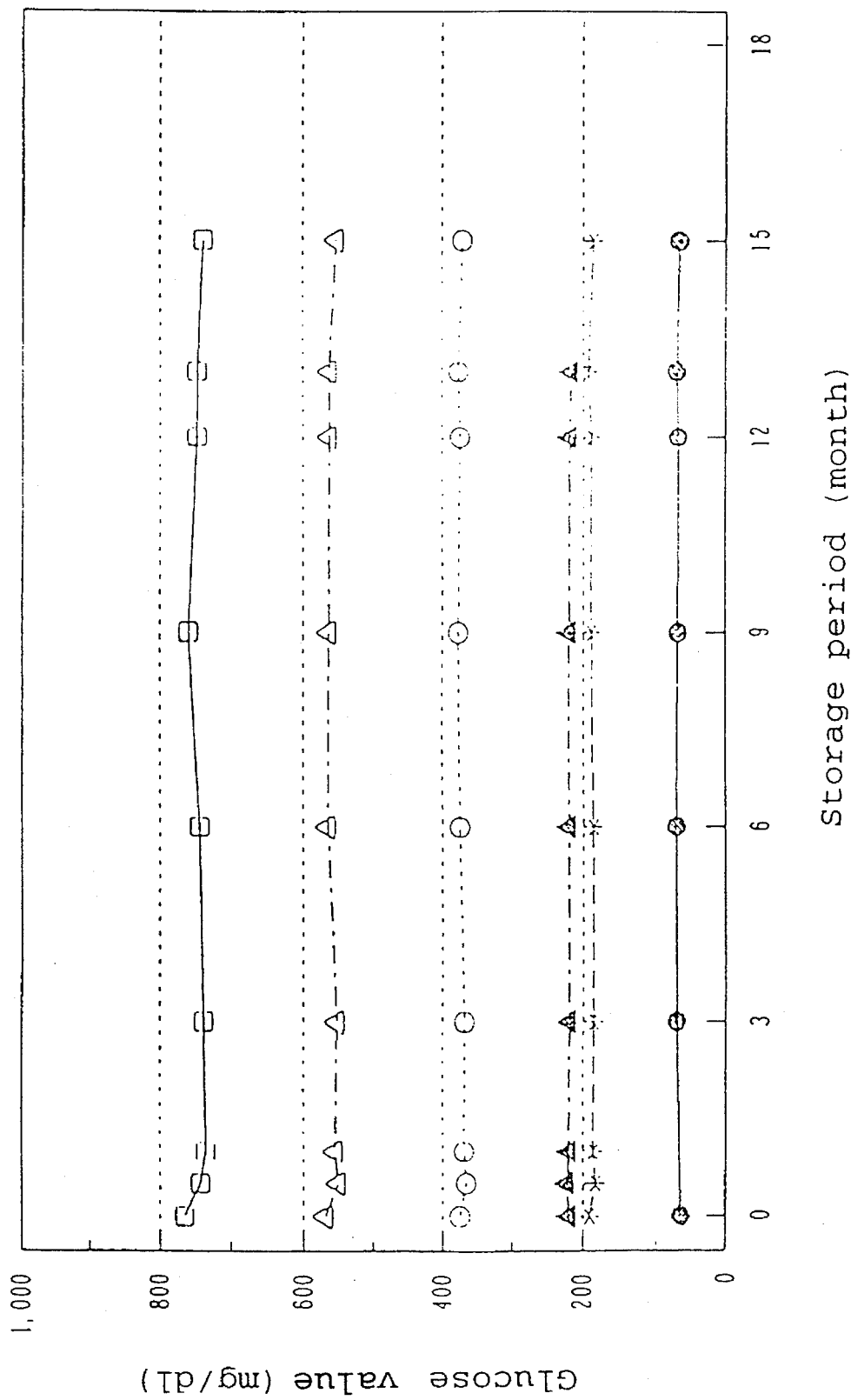
FIG. 2 is a graph showing the stability in the case of storage of the reagent of the present invention at 10° C.

(1) A first reagent and a second reagent of the following compositions were prepared:
First reagent
  62.5 mM tris buffer (pH 9.0)
  31.25 mM potassium chloride
  18.25 mM magnesium chloride
  2.5 mM EDTA
  2.0 mM ATP
  1 U/ml GlcK
  1 U/ml G6PDH
Second reagent
  120 mM acetate buffer (pH 4.0)
  2.5 mM EDTA
  2.5 mM NADP (2) Stability The first reagent and the second reagent prepared in the above item (1) were stored separately at 4° C or 10° C., and were used for automatic analysis of glucose after the elapse of predetermined times. The storage periods before the assay were as shown in FIGS. 1 and 2. For the reagents stored at 4° C., the assays were performed directly after preparation, or after 1 week, 2 weeks, 1 month, 3 months, 6 months, 9 months, 12 months, 13 months, 15 months, or 18 months. For the reagents stored at 10° C., the assays were performed directly after preparation, or after 2 weeks, 1 month, 3 months, 6 months, 9 months, 12 months, 13 months, or 15 months.

As the samples, 4 types of aqueous solutions of glucose (that is, an aqueous solution of 760 mg/dl glucose) (square mark □ in Figures), an aqueous solution of 570 mg/dl glucose (triangle mark △ in Figures), an aqueous solution of 380 mg/dl glucose (circle mark ○ in Figures), and an aqueous solution of 190 mg/dl glucose (asterisk * in Figures) and 2 types of serum (solid circle mark ● and solid triangle mark ▲ in Figures).

The assay procedure comprised adding 320 μl of the first reagent to 3 μl of the sample, incubating the mixture at 37° C for 5 minutes, then adding 80 μl of the second reagent, incubating the mixture at 37° C for 5 minutes, and then measuring the absorption at 340 nm.

The results of the assays are shown in FIG. 1 (reagents stored at 4° C.) and FIG. 2 (reagents stored at 10° C.).

Comparative Example (1) A first reagent and a second reagent of the following compositions were prepared for comparative tests:

First reagent 62.5 mM tris buffer (pH 7.8)

31.25 mM potassium chloride 18.25 mM magnesium chloride 2.5 mM EDTA 2.0 mM NADP

1 U/ml GlcK

1 U/ml G6PDH

Second reagent 100 mM glycine buffer (pH 9.0)

10 mM ATP (2) Stability

Figure 3:
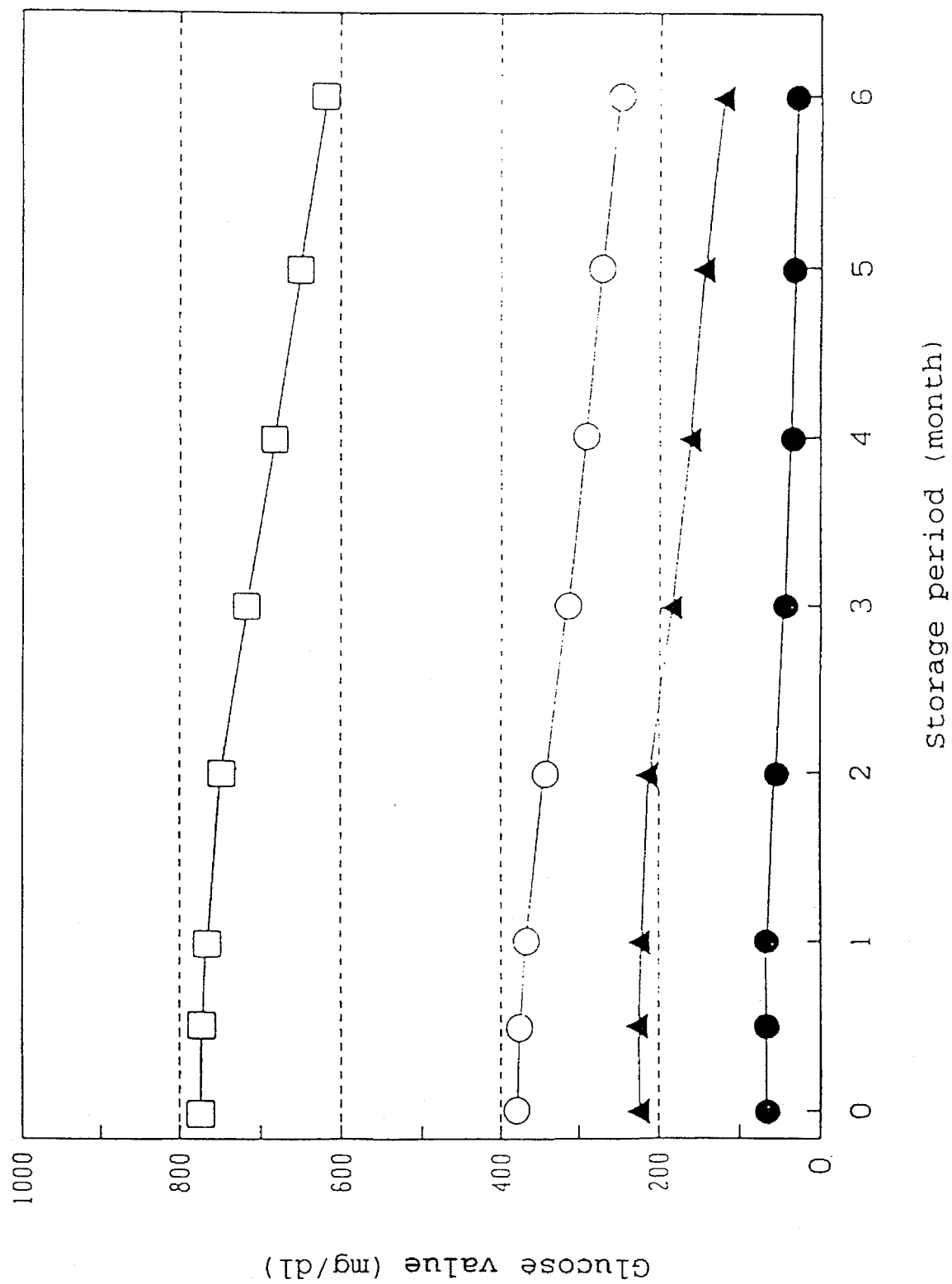
FIG. 3 is a graph showing the stability in the case of storage of a comparative reagent at 4° C.

The first reagent and the second reagent prepared in the above item (1) were stored at 10° C. for comparison. The procedure described in the above Example 1 was performed immediately after preparation, or after 2 weeks, 1 month, 2 months, 3 months, 4 months, 5 months, or 6 months to evaluate the stability of the reagents. The results are shown in FIG. 3. As the samples, 2 types of aqueous solutions of glucose (that is, an aqueous solution of 760 mg/dl glucose (square mark □ in Figure) and an aqueous solution of 380 mg/dl glucose (circle mark ○ in Figure) and 2 types of serum (solid circle mark ● and solid triangle mark ▲ in Figure).

INDUSTRIAL APPLICABILITY

The reagent for assaying glucose of the present invention can be stably stored in a liquid form in a dark or light place, at ordinary temperature to low temperature over a long period (at least 2 years or so). Accordingly, the reagent may be stored for a long period of time at the location performing the clinical examinations and inserted as it is into an automatic analyzer or the like at the time of use without dissolving procedure.

As above, the present invention was explained with reference to particular embodiments, but modifications and improvement obvious to those skilled in the art are including in the scope of the present invention.

We claim:

1. A reagent for assaying glucose in a sample consisting essentially of:

(A) a first reagent containing (i) at least one of glucokinase or hexokinase, (ii) glucose 6-phosphate dehydrogenase and (iii) adenosine 5'-triphosphate, and (B) a second reagent containing an oxidized form of nicotinamide adenine dinucleotide phosphate, wherein said first reagent has a pH of 7.5 to 9.5, said second reagent has a pH of 3 to 5, and both the first reagent and the second reagent are liquids.

2. The reagent according to claim 1, wherein said first reagent contains not less than 0.2 U glucokinase or hexokinase.

3. The reagent according to claim 1, wherein said first reagent contains not less than 0.5 U glucose 6-phosphate dehydrogenase.

4. The reagent according to claim 1, wherein said first reagent contains 0.5 to 5 mM adenosine 5'-triphosphate.

5. The reagent according to claim 1, wherein said first reagent further contains a magnesium salt or chelating agent.

6. The reagent according to claim 1, wherein said second reagent contains 1 to 20 mM of an oxidized form of nicotinamide adenine dinucleotide phosphate.

7. The reagent according to claim 1, wherein said second reagent further contains a magnesium salt.

8. The reagent according to claim 1, wherein buffer concentrations of said first and second reagents are adjusted so that a pH of a mixture of said first and second reagents is 7.5 to 8.5.

* * * * *